US007431916B2

(12) United States Patent
Nilsson et al.

(10) Patent No.: US 7,431,916 B2
(45) **Date of Patent: *Oct. 7, 2008**

(54) ADMINISTRATION OF MEDICINAL DRY POWDERS

(75) Inventors: Thomas Nilsson, Mariefred (SE); Mattias Myrman, Stockholm (SE); Claes Friberg, Akers Styckebruk (SE); Sven Calander, Straengnaes (SE)

(73) Assignee: Mederio AG, Hergiswil NW (CH)

( * ) Notice: Subject to any disclaimer, the term of this patent is extended or adjusted under 35 U.S.C. 154(b) by 321 days.

This patent is subject to a terminal disclaimer.

(21) Appl. No.: 10/603,819

(22) Filed: Jun. 26, 2003

(65) Prior Publication Data

US 2004/0258625 A1 Dec. 23, 2004

(30) Foreign Application Priority Data

Jun. 19, 2003 (SE) .................................... 0301815

(51) Int. Cl.
*A61K 9/00* (2006.01)
*A61K 9/12* (2006.01)
*A61K 9/14* (2006.01)
*A61K 31/46* (2006.01)
*A61K 31/56* (2006.01)
*A61K 47/28* (2006.01)

(52) U.S. Cl. ......................... 424/46; 424/489; 514/169; 514/291; 514/312; 514/649; 514/653; 514/826

(58) Field of Classification Search .................... 424/46
See application file for complete search history.

(56) References Cited

U.S. PATENT DOCUMENTS 5,192,528 A 3/1993 Radhakrishnan et al.
5,437,267 A 8/1995 Weinstein et al.
5,901,883 A 5/1999 Ritsche
5,972,919 A 10/1999 Carling et al.
6,303,103 B1 * 10/2001 Akehurst et al. .............. 424/45

(Continued)

FOREIGN PATENT DOCUMENTS

EP 0 469 814 2/1992

(Continued)

OTHER PUBLICATIONS

"General Remarks" in Purification of Laboratory Chemicals, 4th ed., W. L. F. Amarego and D. D. Perrin, Eds. Elsevier, 1996, p. 1.*

(Continued)

*Primary Examiner*—Johann Richter
*Assistant Examiner*—James H Alstrum Acevedo
(74) *Attorney, Agent, or Firm*—Oblon, Spivak, McClelland, Maier & Neustadt, P.C.

(57) ABSTRACT

A method of administering a metered dry powder combined dose of finely divided dry medication powders is disclosed, wherein said method comprises providing a relative motion between a nozzle of a dry powder inhaler and a dose bed carrying said combined dose of finely divided dry medication powder intended for delivery by the dry powder inhaler, the combined dose comprises metered quantities of at least two medicaments separately deposited on the dose bed, the relative motion causing the nozzle to pass over the combined dose for a simultaneous or sequential delivery of the medicaments during the course of a single suction of air.

15 Claims, 10 Drawing Sheets

U.S. PATENT DOCUMENTS

| | | | | |
|---|---|---|---|---|
| 6,369,115 | B1 | 4/2002 | Ward | |
| 6,422,236 | B1 * | 7/2002 | Nilsson et al. | 128/203.15 |
| 6,698,425 | B1 | 3/2004 | Widerstrom | |
| 2002/0017295 | A1 | 2/2002 | Weers et al. | |
| 2002/0053344 | A1 * | 5/2002 | Davies et al. | 128/203.15 |
| 2002/0103260 | A1 * | 8/2002 | Clarke et al. | 514/630 |
| 2002/0183292 | A1 | 12/2002 | Pairet et al. | |
| 2003/0075172 | A1 | 4/2003 | Johnson et al. | |
| 2003/0109510 | A1 | 6/2003 | Gavin | |
| 2004/0202616 | A1 | 10/2004 | Keller et al. | |
| 2004/0258625 | A1 | 12/2004 | Nilsson | |
| 2005/0042174 | A1 | 2/2005 | Nilsson et al. | |
| 2005/0042175 | A1 | 2/2005 | Nilsson et al. | |
| 2005/0063911 | A1 | 3/2005 | Nilsson et al. | |
| 2005/0103678 | A1 * | 5/2005 | Clark et al. | 206/538 |
| 2005/0175545 | A1 * | 8/2005 | Biggadike et al. | 424/46 |

FOREIGN PATENT DOCUMENTS

| | | | |
|---|---|---|---|
| EP | 1 300 171 | | 4/2003 |
| GB | 2 242 134 | | 9/1991 |
| WO | WO 93/11773 | | 6/1993 |
| WO | WO 98/26828 | * | 6/1998 |
| WO | WO 00/64519 | | 11/2000 |
| WO | WO 00/64520 | | 11/2000 |
| WO | 01/17595 | | 3/2001 |
| WO | WO 01/17595 | | 3/2001 |
| WO | WO 01/39823 | | 6/2001 |
| WO | WO 01/68169 | | 9/2001 |
| WO | WO 01/76601 | | 10/2001 |
| WO | WO 01/78737 | | 10/2001 |
| WO | WO 01/78745 | | 10/2001 |
| WO | WO 02/85281 | | 1/2002 |
| WO | WO 02/11711 | | 2/2002 |
| WO | WO 02/24268 | | 3/2002 |
| WO | WO 03/035137 | | 5/2003 |
| WO | WO 03/061743 | | 7/2003 |
| WO | WO 03/077825 | | 9/2003 |

OTHER PUBLICATIONS

U.S. Appl. No. 10/603,818, filed Jun. 26, 2003, Nilsson.
U.S. Appl. No. 10/603,819, filed Jun. 26, 2003, Nilsson.
U.S. Appl. No. 10/703,505, filed Nov. 10, 2003, Nilsson et al.
U.S. Appl. No. 10/603,819, filed Jun. 26, 2003, Nilsson et al.
U.S. Appl. No. 10/603,819, filed Jun. 26, 2003, Nilsson.
U.S. Appl. No. 10/729,024, filed Dec. 8, 2003, Nilsson et al.
U.S. Appl. No. 10/728,986, filed Dec. 8, 2003, Nilsson et al.

* cited by examiner

ADMINISTRATION OF MEDICINAL DRY POWDERS

TECHNICAL FIELD

The present invention relates to a method of administering medicaments by an oral inhalation route to a user in need of doses comprising at least two therapeutic medicinal dry powders, the doses being packaged to suit a new method of aerosolizing a selected combined dose into air and more particularly, the invention relates to a method of simultaneous delivery in a single inhalation by a user of separate dry powder formulations of different medicaments constituting a combined dose.

BACKGROUND

Administration of drugs by an oral inhalation route is very much in focus today, because of advantages offered like rapid and predictable onset of action, cost effectiveness and high level of comfort for the user. There are mainly two types of inhalers on the market, pressurized metered dose inhalers (pMDIs) comprising a suspension of fine medicament particles in a propellant gas and dry powder inhalers (DPIs) comprising fine medicament particles as dry powder.

Dry powder inhalers (DPI) attract perhaps the most interest, compared to pMDIs, because of the flexibility they offer in terms of nominal dose range i.e. the amount of active substance that can be administered in a single inhalation. So far most development efforts have been directed towards producing effective drugs and formulations for specific abnormal conditions and not so much towards developing the delivery device, i.e. the inhaler.

When inhaling a dose of dry medication powder it is important to obtain by mass a high fine particle fraction (FPF) of particles with an aerodynamic size preferably less than 5 μm in the inspiration air. The majority of larger particles does not follow the stream of air into the many bifurcations of the airways, but get stuck in the throat and upper airways. It is not uncommon for prior art inhalers to have an efficacy of 10-20% only, i.e. only 10-20% of the metered dose by mass is actually delivered as particles with an aerodynamic size less than 5 μm. Since most drugs have undesirable side effects and some may be quite toxic if overdosed, it is important to keep the dosing to the user as exact as possible and to design the delivery system, e.g. an inhaler, such that the efficacy becomes much higher than 10-20%, thereby reducing the required amount of drug in the dose. Also, depending on the targeted site of action, be it systemic or local in the throat and airways, it is desirable to tailor the physical formulation of a medication powder in such a way that it results in an advantageous particle aerodynamic size distribution by mass in the metered dose.

An interesting field of research concerns the possibility of simultaneous administration of combinations of different medicaments. Of course, it is well known in prior art that a successful treatment of a medical condition may is require administration of more than one active substance, e.g. a medicament for relaxing the immediate symptoms like pain or bronchoconstriction and another medicament for treating the underlying abnormal condition like systemic chemical imbalance or airway inflammation respectively. However, it is often difficult to mix the medicaments into a metered dose, because the medicaments may be known to be incompatible or else it is perhaps unknown if and how they interact before they are actually delivered to a subject Therefore, medicaments are generally administered separately, in sequence or by separate routes.

In the past decade research into respiratory diseases, their prophylaxis and treatment, has shown conclusively that simultaneous administration of combinations of different medicaments may improve the clinical condition of patients considerably. In Switzerland patients diagnosed with asthma have been prescribed FORADIL (formoterol, a bronchodilating substance) together with PULMICORT (budesonide, an anti-inflammatory steroid) since the 1980's for treatment of their asthma. Until recently, however, different asthma medicaments have generally been administered separately, in sequence or by separate routes, not in compositions comprising more than one active ingredient. However, there are several published patent applications and approved patents teaching methods of treating respiratory disorders like asthma and chronic obstructive pulmonary disease (COPD) and pharmacologic compositions of different biologic and chemical substances for this purpose, where the combinations offer overall advantages in the treatment of these conditions. See for instance EP 0416950B1 "Medicaments", EP 0416951B1 "Medicaments comprising salmeterol and fluticasone", EP 0613371B1 "New combination of formoterol and budesonid", WO 98/15280 "New combination", WO 00/48587 "Combinations of formoterol and fluticasone propionate for asthma", WO 01/70198A1 "Stabilized dry powder formulations", WO 01/78737A1 "Medical combinations comprising formoterol and budesonid", WO 01/78745A1 "Medical combinations comprising formoterol and fluticasone propionate", WO 02/28368A1 "New combination for the treatment of asthma", WO 03/013547A1 "Pharmaceutical composition comprising salmeterol and budesonid for the treatment of respiratory disorders". However, the quoted documents deal with aspects of formulating, processing, stabilizing and using mixtures of at least two ingredients. The chemical compositions and mixing ratios between active ingredients are generally focused upon, not methods of administration of such compositions or devices for that purpose. It is, however, difficult to mix dry medicament powders and optional excipients in a certain proportion consistently. The proportions in such a metered combined dose cannot be easily controlled, because the ratio of medicaments in an individual, combined dose depends significantly on the particle forces existing in each medicament powder, between particles of different medicaments and between medicament powders and dose packaging materials. Hence, actual variations in the ratio between active ingredients from combined dose to combined dose may be too large, causing serious problems if a potent ingredient is delivered in a higher or lower amount than expected.

Thus, there is room for improvements regarding methods and devices for simultaneous administration of different medicaments, which combine advantageously in treatment of certain medical disorders.

SUMMARY

A method of administering metered dry powder combined doses of finely divided dry medication powders is disclosed. A metered dry powder medicinal combined dose comprising at least two medicaments of separate dry powder formulations is prepared, whereby a metered powder quantity per medicament is deposited in a dose forming step, where the sum of the depositions constitute the metered quantity of powder in the medicinal combined dose. The deposits of the at least two medicaments are suitably kept separated from each other, such that the medicaments cannot detrimentally interact after forming of the combined dose, and the medicinal combined dose can be introduced into an inhaler device for a delivery of the medicinal combined dose during the course of a single inhalation, whereby the delivered medicinal combined dose is composed to a high degree by mass of de-aggregated fine particles of each of the at least two medicaments.

Furthermore a therapeutic metered medicinal, combined dosage of finely divided dry medication powders is disclosed wherein the therapeutic, metered combined dosage comprises metered quantities of at least two medicaments, separately deposited; and the medicinal combined dosage is adapted for a user initiated delivery of the combined dosage during the course of a single inhalation through an inhaler device. The at least two medicaments of the medicinal combined dosage are aerosolized generally simultaneously or generally sequentially during an inhalation, depending on how the dosage is physically composed, whereby a delivered dosage to a user consists of a high degree by mass of fine particles of each medicament such that a large proportion of each medicament settles in the intended target area in the airways and lungs of the user.

BRIEF DESCRIPTION OF THE DRAWINGS

The invention, together with further objects and advantages thereof, may best be understood by referring to the following detailed description taken together with the accompanying drawings, in which.

DETAILED DESCRIPTION

Figure 1:
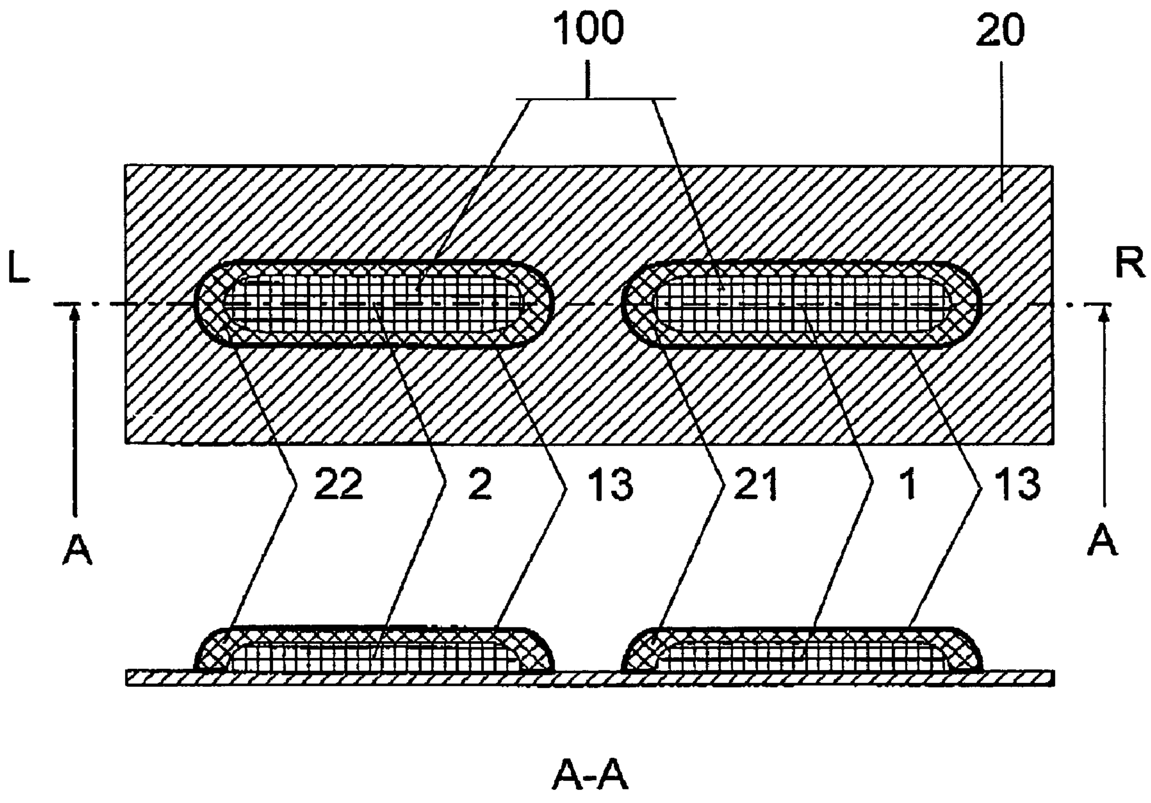
FIG. 1 illustrates in top and side views a first embodiment of combined doses comprising two medicament deposits in separate compartments onto a dose bed.

The present invention is based on a new method of forming combined doses comprising more than one medicament deposited onto a dose bed and a new method of delivering such combined doses by an inhalation route to a user of a dry powder inhaler (DPI).

In the context of this application the word "medicament" is defined as a pharmacological substance, which comprises at least one chemically or biologically active agent. Further, a medicament may exist in a pure form of one or more pure active agents, or a medicament may be a compound comprising one or more active agents, optionally formulated together with other substances, e.g. enhancers, carriers, diluents or excipients. From this point on, the term "excipient" is used to describe any chemical or biologic substance mixed in with a pure active agent for whatever purpose. In this document, only medicaments in dry powder form are discussed.

A "dose bed" is henceforth defined as a member capable of harboring a metered dose of one or more dry powders, where the dose is intended for a delivery to a user of a DPI in a single inhalation performed by the user. In the present invention a combined dose comprises metered deposits of at least two medicaments. The dose bed may be divided in several areas or incorporate two or more compartments intended for deposits of dry powders. In a preferred embodiment the combined dose is packaged for a continuous, prolonged delivery, i.e. the delivery period is in a range 0.01 to 6 s, usually in a range 0.1 to 2 seconds, delivery taking place sometime during the course of an inhalation as controlled by a purposefully designed DPI. Advantageously, such a DPI adopts an Air-razor method of gradual aerosolization of the combined dose comprising introduction of a relative motion between an air-sucking nozzle and the powder dose. Advantages of a prolonged delivery of a dose for inhalation are disclosed in our U.S. Pat. No. 6,571,793 (WO 02/24264 A1), which is hereby incorporated in this document in its entirety as a reference.

A preferred embodiment of a metered combined dose uses a dose bed split up in at least two separate compartments, where each compartment is intended for a metered deposition of a particular medicament. Each compartment containing a metered amount of a specified medicament powder may then be sealed, e.g. by foiling, such that the different medicaments in the different compartments of the dose bed cannot interact in any way and can not be contaminated by foreign substances or moisture. Alternatively, a common foil encloses all compartments, but sealing between compartments may be excluded if individual sealing is not a requirement. A dose carrier is normally engaged to carry at least one dose bed loaded with a dose, whereby the dose carrier may be inserted into a DPI for administering a combined dose or doses sequentially to a user in need of treatment. A suitable carrier of doses is disclosed in our Swedish patent publication SE 0517 806 C2 (WO01/34233 A1), which is hereby incorporated in this document in its entirety as a reference. However, a dose bed may be designed to act as a carrier, intended for direct insertion into a DPI. A suitable DPI for a continuous dose delivery is disclosed in our U.S. Pat. No. 6,422,236 B1, which is hereby incorporated in this document in its entirety as a reference.

If complete physical separation of the deposits of the different medicaments making up the combined dose is not required, but some degree of overlap or mixing is acceptable from a physical, chemical and medical point of view, then other methods of separating the deposits may be implemented. Depending on what degree of mixing is permitted different ways of separating deposits must be adopted. For example, in one embodiment, the different medicaments may be deposited in parallel strings onto the dose bed. The dose bed may use separate indentations where the powder should be deposited, but flat target areas for deposits in a single plane on the dose bed are equally possible. In another embodiment the different medicaments are deposited sequentially dot-wise or string-wise onto different target areas of the dose bed. Yet another way of depositing the medicaments would be on top of one another, in layer by layer, such that each medicament is deposited on top of the previously deposited one. If necessary, to stop chemical or biological interaction or decomposition caused by, for example, adjacent medicament powders being incompatible, an isolating layer of a biologically acceptable, inert substance like carbohydrates, e.g. glucose or lactose, may be deposited between adjacent layers of medicament. A similar method of separation may also be used to positively separate adjacent dots or strings of medicaments, by depositing an inert substance between adjacent dots or strings of different medicament deposits onto the dose bed. When the combined dose has been completely formed it is usually sealed from ingress of dirt and moisture by a foil covering the entire dose bed. A method of depositing microgram and milligram quantities of dry powders using electric field technology is disclosed in our U.S. patent application Ser. No. 2003/0012865 A1, which is hereby incorporated in this document in its entirety as a reference.

Forming a combined dose comprising at least two medicaments in separate dry powder formulations may be done in different ways, known in prior art. The invention discloses that the components of the combined dose, i.e. the at least two medicaments need not be mixed or processed together prior to dose forming and, indeed, should normally be kept separated during dose forming as well as after the combined dose is formed and sealed. The medicaments of the combined dose are thus kept separated on the dose bed by a suitable method, as described in the foregoing, until the combined dose is about to be delivered by an inhalation route to a user.

Methods of dose forming include conventional mass or volumetric metering and devices and machine equipment well known to the pharmaceutical industry for filling blister packs, for example. See European Patent No. EP 0 319 131 B1 and U.S. Pat. No. 5,187,921 for examples of prior art in volumetric and/or mass methods and devices for producing doses of medicaments in powder form. Electrostatic forming methods may also be used, for example as disclosed in U.S. Pat. No. 6,007,630 and U.S. Pat. No. 5,699,649. Any method capable of producing metered micro- and milligram quantities of dry powder medicaments may be used, even completely different methods may be applied to suit the different medicaments selected to be part of the combined doses to be produced. Total mass in a combined dose according to the present invention is typically in a range from 50 μg to 50 mg. Regardless of which forming and filling method is being used for a particular medicament, it is important during dose forming to make sure that intended medicaments are individually metered and deposited onto their respective target areas or compartments of the dose bed. The target areas or compartments of the dose bed, which combine to hold a dose, may be of same or differing sizes. The shape of compartments is governed by physical constraints defined by the type of dose bed used. As an example, a preferred type of dose bed is an elongated strip of a biologically acceptable, inert material, e.g. plastic or metal, between 5 and 50 mm long and between 2 and 10 mm wide. The strip is further divided in separate target areas or compartments arranged along the length of the elongated strip. The dose bed or, if necessary each compartment, receives an individual seal, for instance in the form of a foil, in a step immediately subsequent to the dose forming.

An advantage of the present invention is that a potentially interesting medicament may be individually selected on merits of its own for inclusion in a combined dose, in disregard of whether or not it is chemically or biologically compatible with other potentially interesting medicaments. The combined dose may be designed to include medicaments, which have proven medical effects of different, desirable kinds, even though the selected medicaments may be chemically or biologically incompatible or unstable in the form of a mixture. Thus, the regulatory process before introducing combined doses of medicament combinations on the market may be drastically simplified. Yet another advantage of the invention is the possibility of using pure, more or less potent medication substances as selected medicaments of the combined dose, without included excipients. Non-exclusive, illustrative examples not limiting the scope of the invention of suitable typical medicaments for treatment of asthma and COPD to be combined in single combined doses in accordance with the present invention are listed below:

Formoterol and Budesonide
Formoterol and Ipratropium
Formoterol and Fluticasone
Formoterol and Tiotropium
Ipratropium and Budesonide
Ipratropium and Salbutamol Illustrative examples, not limiting the scope of the invention and analogous with respiratory medicaments of suitable medicaments for pain control, which may be advantageously combined to be combined in single combined doses according to the present invention, include non-exclusively:

Almotriptan
Analgesics
Anticonvulsants
Antidepressants
Antiemetics
Aspirin (lysine acetylsalicylic acid)
Betablockers
Calcium channel antagonists
Codeine
DHE
Domperidone
Eletriptan
Ergotamine
Frovatriptan
Metoclopramide
Naratriptan
Isometheptene
Opiates
Paracetamol
Rizatriptan
Serotonin
Sumatriptan
Triptans
Zolmitriptan Optimal dosages of the respective active substances for prevention or treatment of disorders may be determined by those skilled in the art, and will vary with the type of disorder, selected compounds and their respective potency, and the advancement of the disease condition. Furthermore, factors associated with the individual undergoing treatment determine correct dosages, such as age, weight, sex etc. Depending on what are correct dosages, the correct deposits by mass for the prepared medicaments may be calculated, such that metered deposits of each medicament to be included in the metered combined dose may be produced in a dose-forming step. In calculating a correct nominal deposit of mass for each medicament component the fine particle fraction, i.e. particles having a mass median aerodynamic diameter (MMAD) less than 5 μm, per component of the actual delivered dose must be taken into consideration. As discussed in the foregoing, the efficacy of inhalers differs considerably and it is thus important to include the expected efficacy of the chosen inhaler in the calculation of what is a suitable nominal mass deposit. Another parameter to consider when forming the combined dose is the physical formulation of included medication powders. Formulation objectives may differ for the different medicament components of the combined dose. The particle aerodynamic size distribution by mass may be targeted differently for the different dose components in order to optimize the efficacy of each component in the treatment of a particular disease in a host user. For instance, the MMAD for a steroidal medicament component should be larger than that of a bronchodilating medicament component. Whereas maximum penetration into the lungs is required of a bronchodilator, a minimum of systemic absorbance and maximum local deposition in the targeted area of the airways is required of the steroid.

Compared to prior art, more opportunities are opened up by the present invention in selecting medicaments based on existing compositions with proven medical effects, rather than first developing a mixture or formulation of different medicaments and then proving that the new combination is effective, stable and lacks serious side effects. The present invention makes it possible to define combined doses using any combination of pure medicaments, i.e. pure pharmacologic agents, and medicaments comprising excipients. A combined dose thus formed onto a dose bed may be introduced into a dry powder inhaler (DPI) such that the medicament components making up the combined dose may be aerosolized and delivered in the inspiration air during the course of an inhalation through the DPI by a user.

The invention also offers interesting opportunities for combinations of new medicaments and combinations of new medicaments with existing, proven ones. Keeping the different medicaments separated according to the invention may reduce the investment in time and resource necessary for getting the combined medicaments approved by the relevant regulatory bodies and released to the respective markets. For instance, no added substance to stabilize the combined product will be needed and no testing to prove that the added substance is harmless needs be performed. New areas of therapy are thus now suitable for treatment by inhalation. Besides asthma, COPD and pain, other examples not limiting the scope of the invention, of medical areas of therapy, where combinations of medicaments administered in single combined doses by an inhalation route may improve the quality of treatment, lower the costs and make life for patients more comfortable, are non-exclusively:

Disorders of the alimentary tract or the digestive system
Disorders of the cardiovascular system
Disorders of the endocrine system
Disorders of the respiratory system
Genital or sexual disorders
Disorders of the muscular or neuromuscular system
Disorders of the
Psychosomatic disorders
Anti-infectives
Allergic disorders
Protective or antinoxious agents The present invention differs from prior art inhalers and related dose delivery methods by providing a combined dose comprising two or more separate medicaments, more or less separately deposited onto a dose bed. The combined dose is therefore not a composition of medicaments constituting a single physical entity, but rather two or more physical entities contained in a single dose. Inserted into a DPI, the combined dose will be aerosolized such that the entities of the dose, i.e the medicaments, are delivered mostly sequentially or optionally mostly simultaneously into the inspiration air during an inhalation by a user. Whether medicaments included in a combined dose are aerosolized mainly sequentially or mainly simultaneously depends partly on the physical form of the combined dose, i.e. how the medicament deposits are interrelated and partly on what type of inhaler is used to administer the combined dose. It is obvious that an inhaler, which subjects all of the combined dose to a jet-stream of air will aerosolize the included deposits simultaneously and more or less mixed, whereas an inhaler subjecting the combined dose to a jet stream gradually, like a moving tornado, thereby not attacking all of the combined dose at once, nay aerosolize the deposits of the dose gradually over time. An object of the invention is to offer better control of combined dose release and to facilitate a prolonging of the dose delivery in order to produce a high fine particle fraction (FPF) in the delivered, combined dose. Another object of the invention is to achieve a high ratio of delivered, combined dose relative metered combined dose. Although it is possible to successfully apply the invention to prior art inhalers, these tend to deliver the dose in too short a time, resulting in a poor FPF figure and low efficacy. On the other hand, a gradual dose delivery is possible using a new inhaler design where a relative movement is introduced between the dose and a suction nozzle through which the inspiration airflow is channeled. This arrangement utilizes the inhalation effort of the user to aerosolize the combined dose gradually for a prolonged period, thus using the power of the suction more efficiently and eliminating in most cases a need for external power to aerosolize the combined dose.

A powder Air-razor method is advantageously used for aerosolizing the medicament powders in the combined dose, the Air-razor providing de-aggregation and dispersal into air of the finely divided medication powders. Utilizing an effort of sucking air through a mouthpiece of an inhaler, said mouthpiece connected to a nozzle, the particles of the deposited medicament powders, made available to the nozzle, are gradually de-aggregated and dispersed into a stream of air entering the nozzle. The gradual de-aggregation and dispersal is produced by the high shearing forces of the streaming air and a relative motion introduced between the nozzle and the powders of the combined dose. In a preferred embodiment, the medicament powders are deposited onto a dose bed, such that the powder deposits occupy a larger area than the area of the nozzle inlet. The nozzle is preferably positioned outside the deposited area, not accessing the powder by the relative motion until the air stream into the nozzle, created by the suction, has passed a threshold flow velocity. Coincidental with the application of the suction or shortly afterwards the relative motion will begin such that the nozzle traverses the powder dose gradually. The high velocity air going into the nozzle inlet provides plenty of shearing stress and inertia energy as the flowing air hits the leading point of the border of the contour of the first medicament deposit. This powder Air-razor method, created by the shearing stress and inertia of the air stream, is so powerful that the particles in the particle aggregates in the powder adjacent to the inlet of the moving nozzle are released, de-aggregated to a very high degree as well as dispersed and subsequently entrained in the created air stream going through the nozzle. If the medicament deposits have been made in separate compartments of the dose bed and individually sealed, then obviously the compartments must be opened up first so that the nozzle can access the deposited powder in each compartment when suction is applied. Naturally, this is also true if the deposits share a common seal without an individual seal for each deposit. An arrangement for this purpose is disclosed in our Swedish patent publication SE 517 227 C2 (WO 02/24266 A1), which is hereby incorporated in this document in its entirety as a reference. Depending on how the deposits are laid out on the dose bed, the nozzle will either suck up the deposits sequentially or in parallel or in some serial/parallel combination.

Thus, the quality of combined dose delivery is dramatically improved compared to prior art performance, and leading to important advances in delivering a majority of fine particles of the medicaments of the combined dose to the intended target area or areas in the user's airways and lungs with very little loss of particles settling in the throat and upper airways. Administering medicament combinations according to the present invention has a very positive therapeutic effect from a medical, psychological and social point of view on a host in need of treatment with a combination of at least two medicaments.

DETAILED DESCRIPTIONS OF DRAWINGS

Referring to reference numbers 1-100 of the drawings wherein like numbers indicate like elements throughout the several views of ten different embodiments of a combined dose comprising at least two deposits of at least two medicaments onto a dose bed as illustrated in FIGS. 1-10 presented here as non-limiting examples.

FIG. 1 illustrates a combined dose 100 comprising two different medicament deposits, 1 and 2, in separate compartments 21 and 22 onto a dose bed 20, which may be capsules or blisters or moldings in the dose bed. An individual seal 13 for each compartment guarantees that the medicaments cannot be contaminated by foreign matter or by one another. The illustrated deposits are intended for a sequential delivery taking place during an inhalation.

Figure 2:
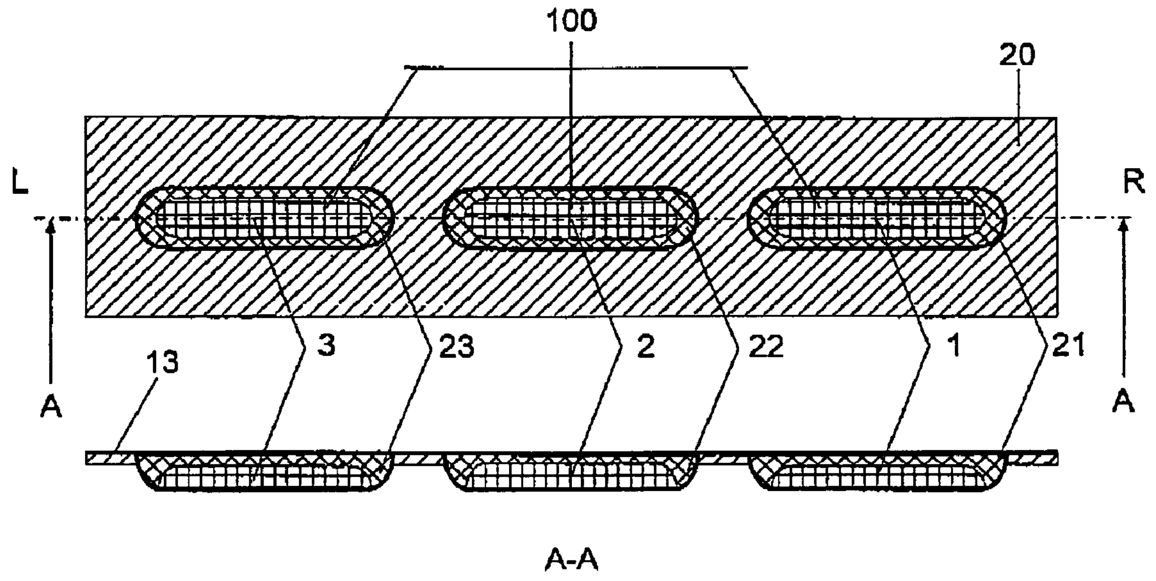
FIG. 2 illustrates in top and side views a second embodiment of combined doses comprising three medicament deposits in separate compartments onto a dose bed.

FIG. 2 illustrates a combined dose 100 comprising three different medicament deposits, 1, 2 and 3 in separate compartments 21, 22 and 23 similar to FIG. 1, but arranged underneath the dose bed 20. Besides a different arrangement of compartments on the dose bed 20 and the respective seals 13, the main difference between FIG. 1 and FIG. 2 is that deposit 3 may consist of a different medicament from deposits 1 and 2 is or it may consist of either the medicament of deposit 1 or 2. It is thus possible not only to administer more than one medicament, but also to compose combined doses of e.g. two medicaments with a very high ratio of mass between them. The illustrated deposits are intended for a sequential delivery taking place during an inhalation.

Figure 3:
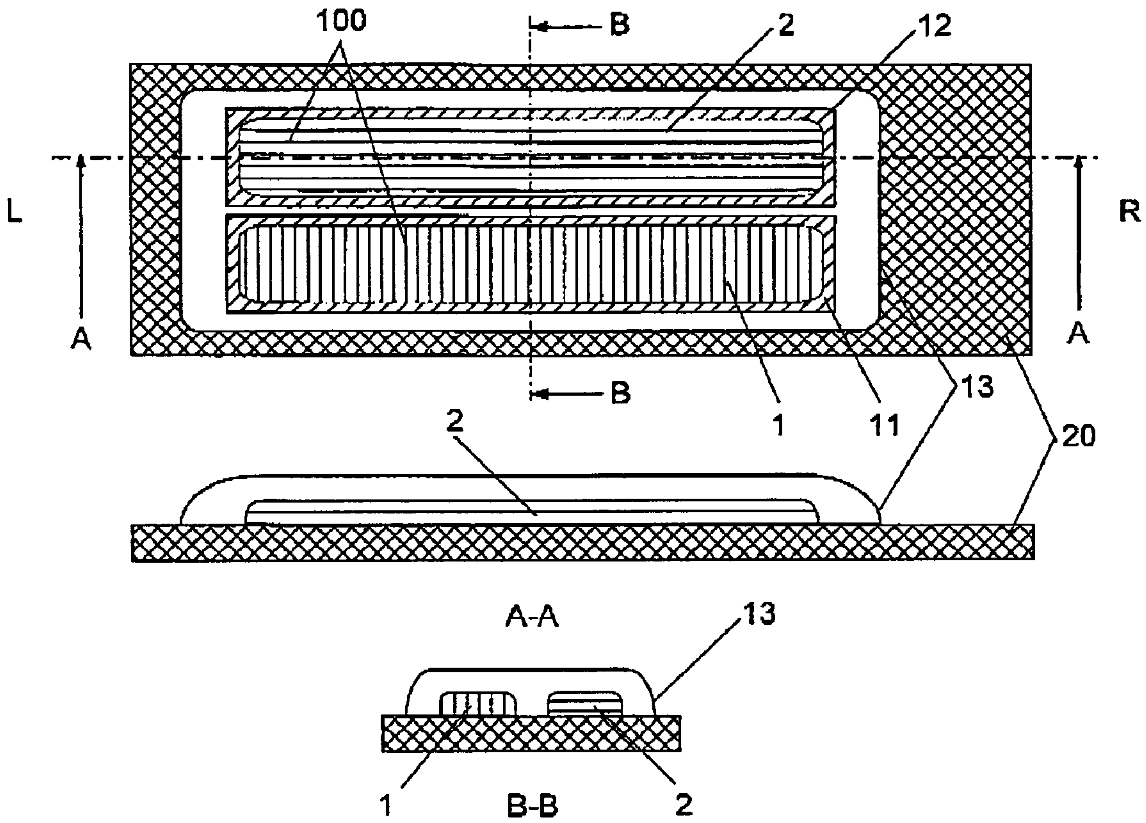
FIG. 3 illustrates in top and side views a third embodiment of combined doses comprising two parallel medicament deposits onto a dose bed.

FIG. 3 illustrates a combined dose 100 comprising two different medicament deposits, 1 and 2, laid out in parallel strips onto separate target areas 11 and 12 respectively onto the dose bed 20. A common protective foil 13 protects the medicaments of the combined dose from being contaminated by foreign matters. The illustrated deposits are intended for a fully simultaneous delivery of the two medicaments taking place during an inhalation.

Figure 4:
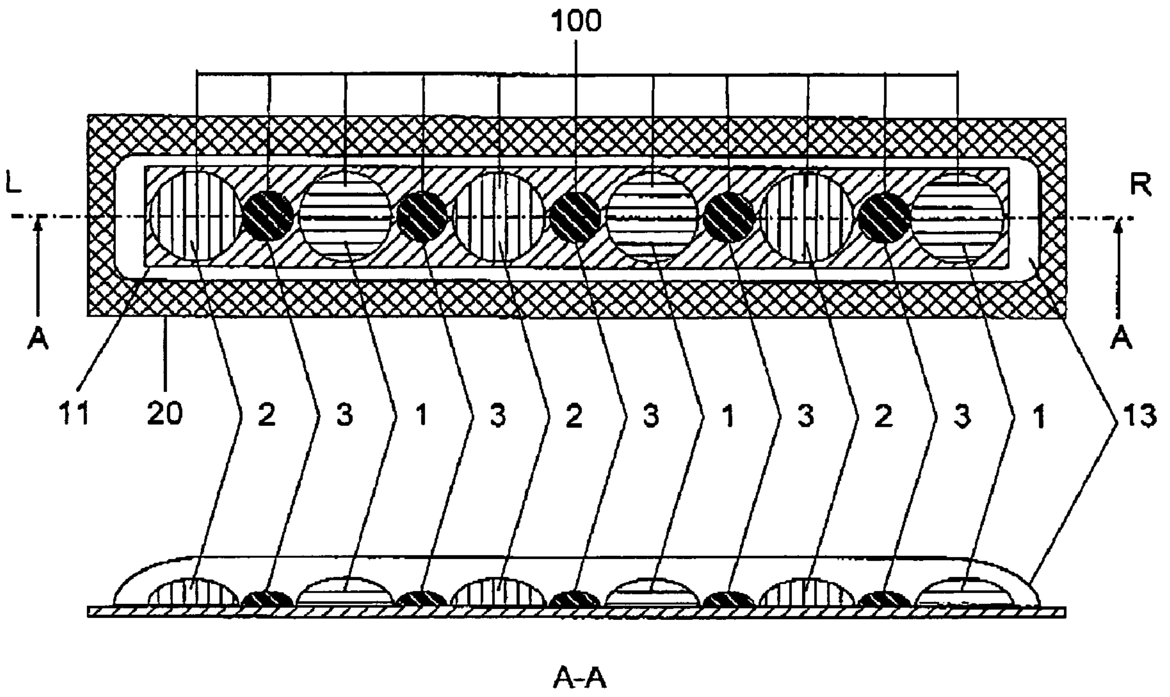
FIG. 4 illustrates in top and side views a fourth embodiment of combined doses comprising several medicament deposits and separating excipient deposits onto a dose bed.

FIG. 4 illustrates a combined dose 100 comprising two different medicaments, 1 and 2, each comprising several deposits separated by deposits of an inert excipient 3. The deposits are laid out in a string of spots onto a target area 11 on a dose bed 20. The deposits share a common seal 13. The combined dose is intended for a sequential delivery of incorporated medicament spots, said delivery taking place during an inhalation. The excipient deposits help to minimize unintentional mixing of the medicaments. If some mixing of medicaments can be accepted, then the excipient may be left out altogether. Combined doses composed of spot deposits may of course comprise more medicaments than two. The mass ratio between medicaments may be easily set by controlling the ratio between the number of spots per medicament in combination with the size of the respective spots in terms of deposited mass. Naturally the spots need not necessarily be circular in shape, they may take an elongated or elliptical form, depending on which type of dose forming method is used.

Figure 5:
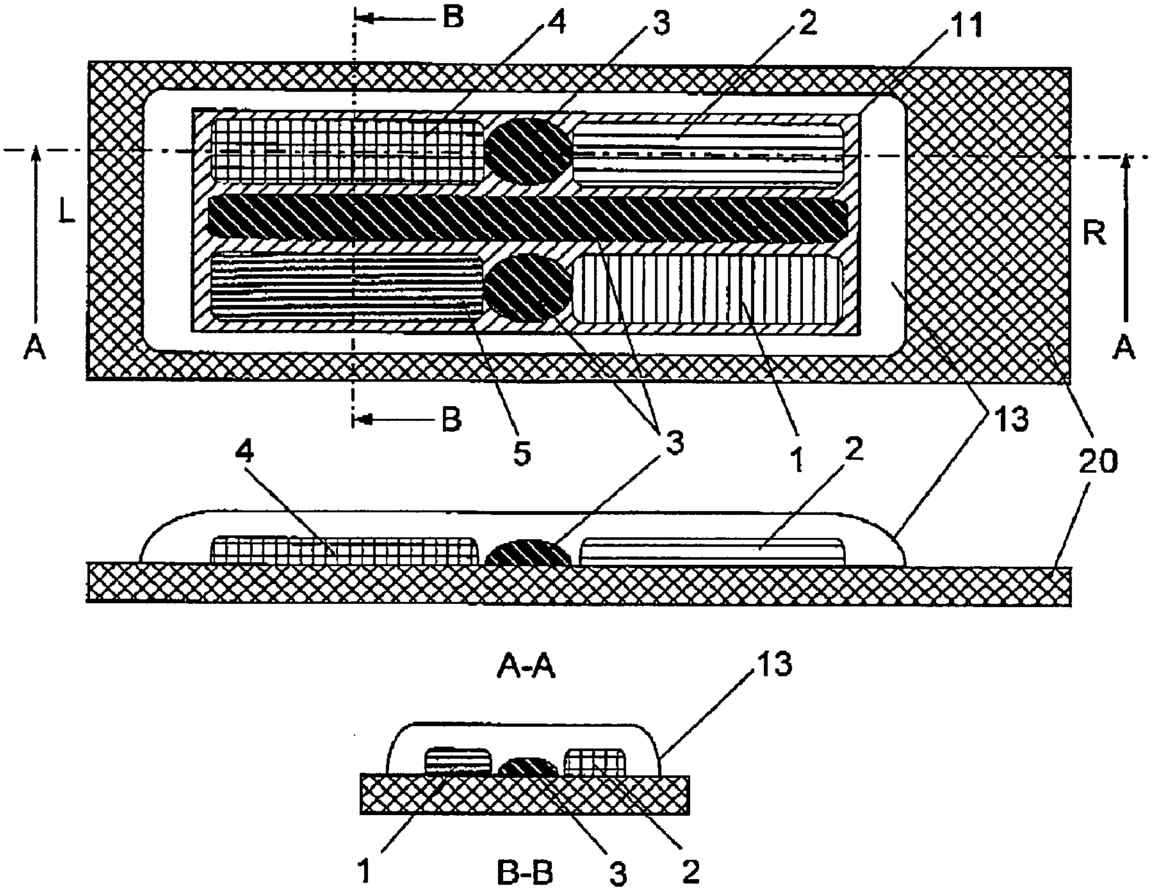
FIG. 5 illustrates in top and side views a fifth embodiment of combined doses comprising four medicament deposits and separating excipient deposits onto a dose bed.

FIG. 5 illustrates a combined dose 100 comprising deposits of four different medicaments, 1, 2, 4 and 5, separated by deposits of an inert excipient 3. The deposits are laid out in two parallel groups of two in-line strips of medicament onto a common target area 11 on a dose bed 20. The deposits share a common seal. The excipient deposits help to minimize unintentional interaction of the medicaments. The combined dose is intended for a combined parallel/simultaneous and sequential delivery of incorporated medicament strips, said delivery taking place during an inhalation.

Figure 6:
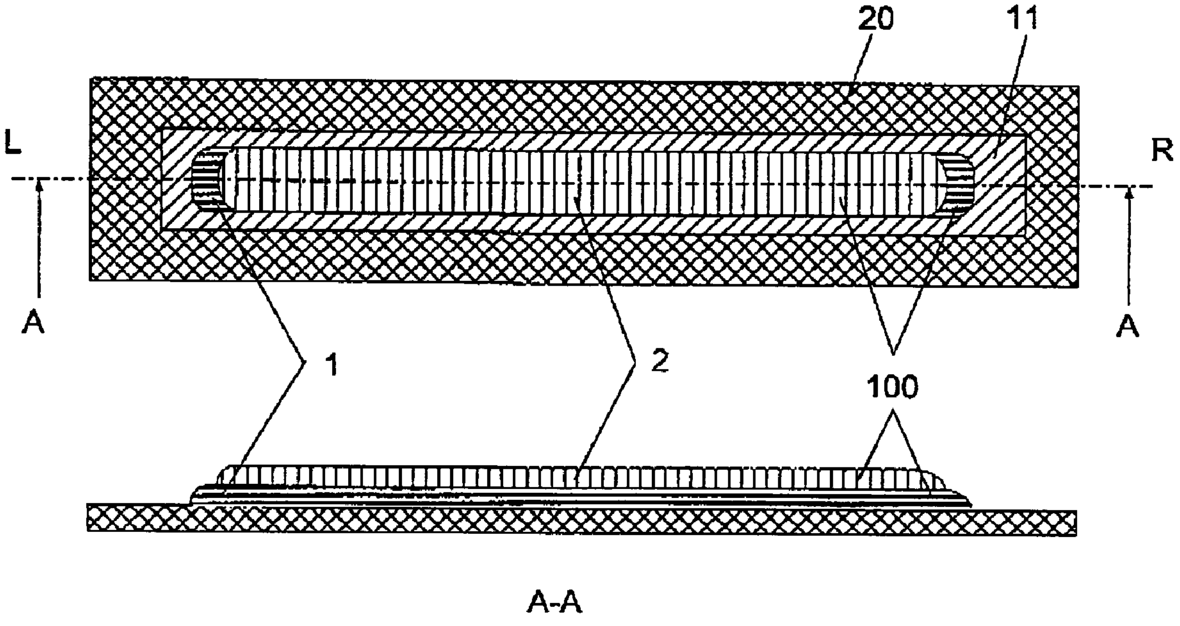
FIG. 6 illustrates in top and side views a sixth embodiment of combined doses comprising two parallel medicament deposits on top of one another onto a dose bed.

FIG. 6 illustrates a combined dose 100 comprising two different medicaments, 1 and 2, each comprising a strip of deposited powder, medicament 1 deposited onto a target area 11 of a dose bed 20 and medicament 2 deposited on top of the deposit of medicament 1. This method of dose forming is an alternative to the ones previously disclosed and may be used when a certain level of interaction of the medicaments can be tolerated.

Figure 7:
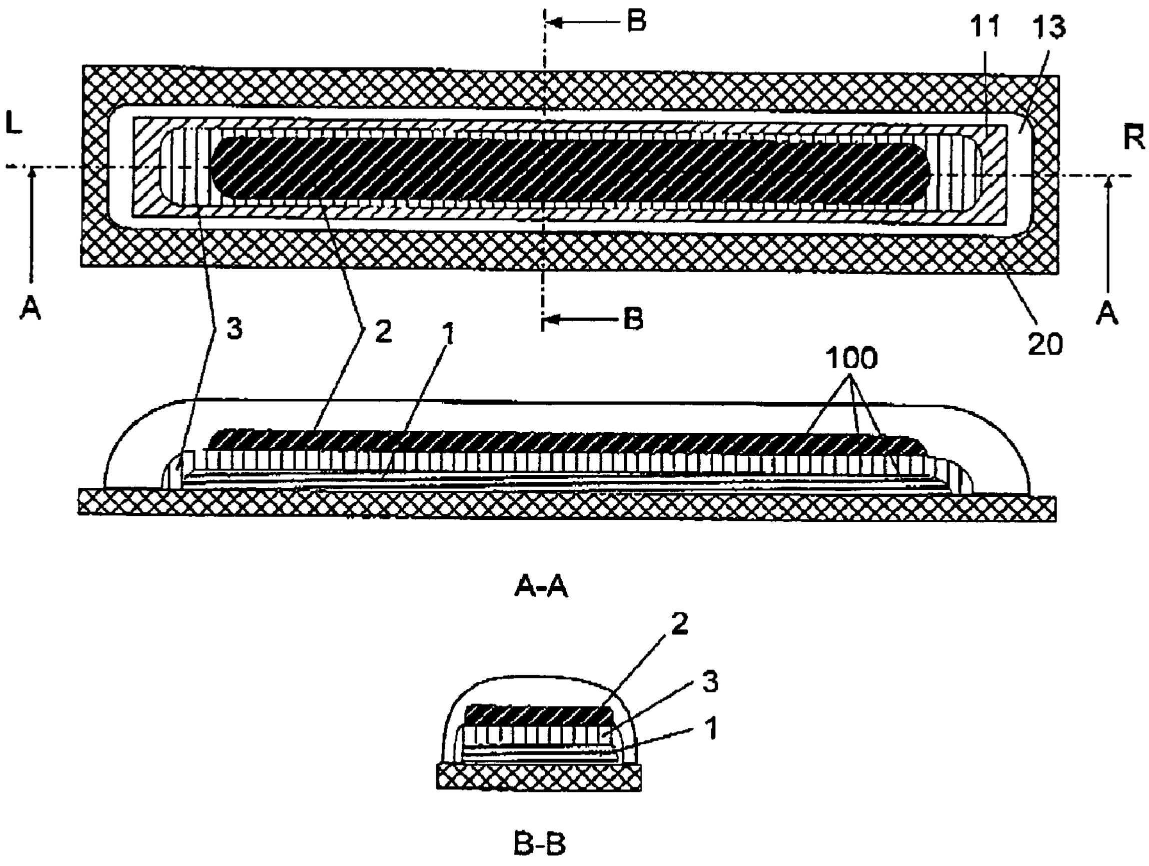
FIG. 7 illustrates in top and side views a seventh embodiment of combined doses comprising two medicament deposits on top of one another onto a dose bed, but separated by a deposit of an excipient.

FIG. 7 illustrates a combined dose 100 comprising two different medicaments, 1 and 2, and an excipient 3, each comprising a strip of deposited powder. Medicament 1 is deposited onto a target area 11 of a dose bed 20 and excipient 3 is deposited onto medicament 2 to insulate medicament 1 from a deposit of medicament 2 on top of the deposits of medicament 1 and excipient 3. This way of forming doses is not restricted to include only two medicaments, but several medicaments may be deposited on top of one another, if necessary with an insulating deposit of excipient between layers.

Figure 8:
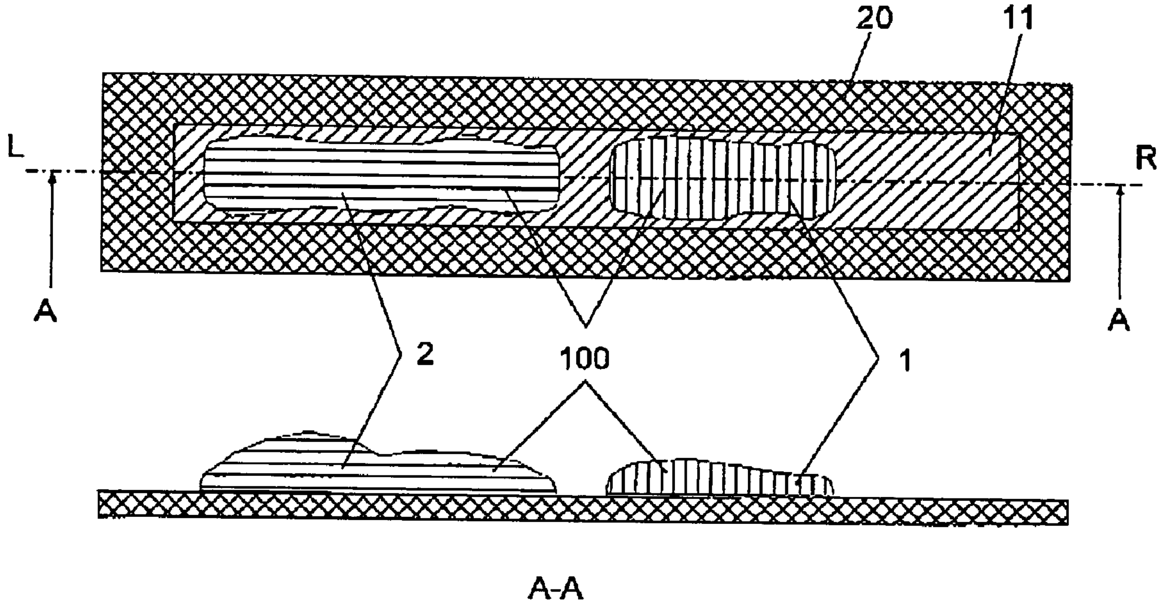
FIG. 8 illustrates in top and side views another embodiment of a combined dose comprising two medicaments separately deposited onto a dose bed.

FIG. 8 illustrates a combined dose 100 comprising two different medicament deposits, 1 and 2, of somewhat irregular shapes but separately laid out onto a common target area 11 of the dose bed 20. The illustrated deposits are intended for a sequential delivery of the two medicaments taking place during an inhalation.

Figure 9:
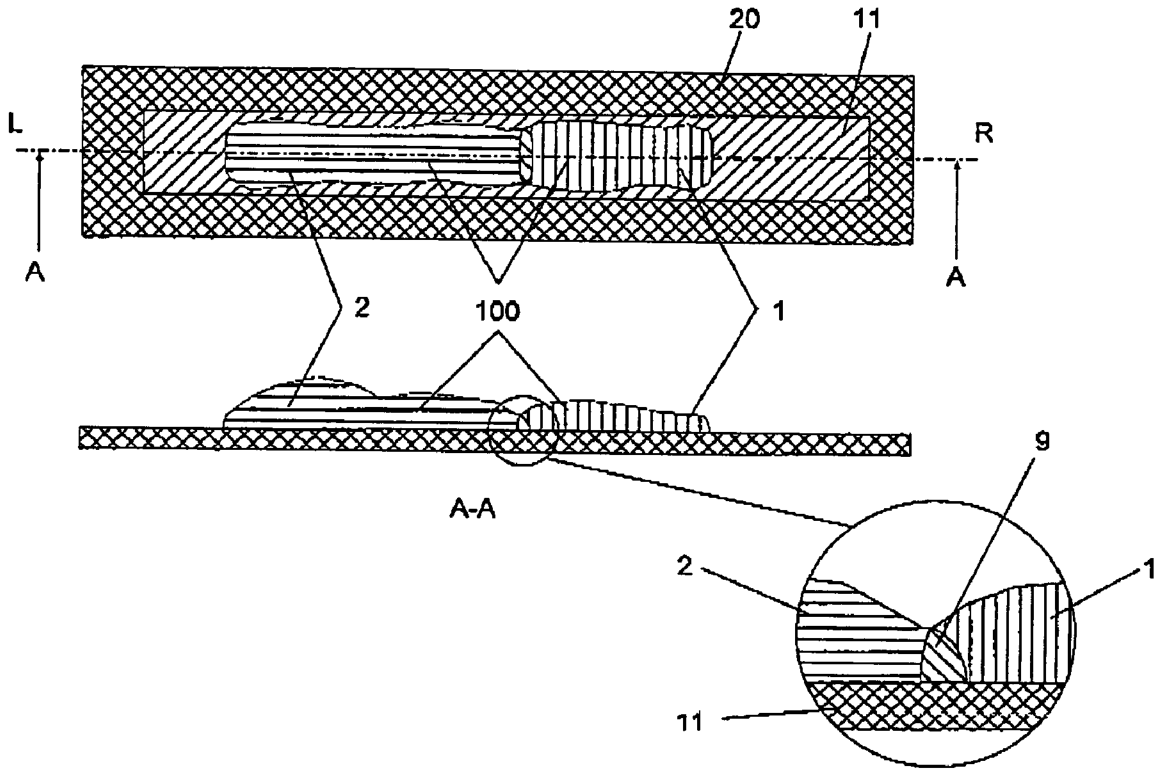
FIG. 9 illustrates in top and side views yet another embodiment of a combined dose comprising two medicaments separately deposited onto a dose bed, but with some degree of overlap.

FIG. 9 illustrates a combined dose 100 comprising two different medicament deposits, 1 and 2, of somewhat irregular shapes but generally separately laid out onto a common target area 11 of the dose bed 20. The illustrated deposits overlap slightly, resulting in a arbitrary mixture 9. The deposits are intended for a mostly sequential delivery of the two medicaments taking place during an inhalation.

Figure 10A:
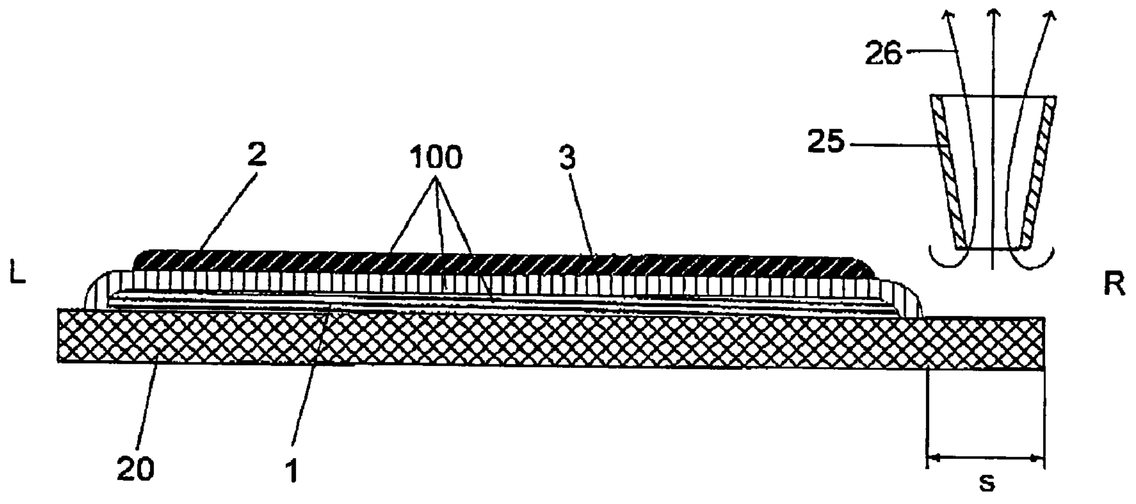
FIG. 10*a* illustrates in a sectional view an example of a combined dose comprising two medicament deposits on top of one another but separated by a deposit of an excipient onto a dose bed and adjacent to tie combined dose a nozzle in a starting position before the combined dose is released.
Figure 10B:
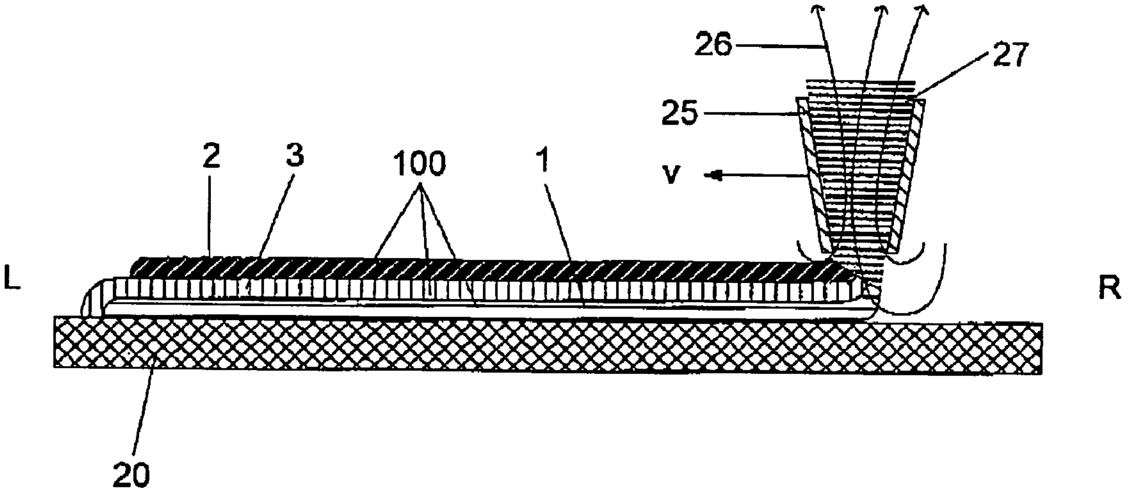
FIG. 10*b* illustrates in a sectional view an example of a combined dose comprising two medicament deposits on top of one another but separated by a deposit of an excipient onto a dose bed and adjacent to the combined dose a nozzle in a relative motion sucking up the powder particles to be dispersed into the air stream.

FIGS. 10*a* and 10*b* illustrate a delivery of a combined dose 100 comprising two different medicaments, 1 and 2, and an excipient 3, each comprising a strip of powder sequentially deposited in three different layers. A nozzle 25 with an established flow of air 26 going into it is put in a relative motion, parallel to the dose bed 20, such that the nozzle passes over the combined dose beginning at the right side R and ending at the left side L of the dose bed. This Air-razor method results in a simultaneous, gradual delivery of medicaments 1 and 2 together with the excipient 3. The powders of the deposits are mixed into an aerosol 27 by the air flowing into the nozzle leading to simultaneous delivery of the two medicaments and the excipient. This Air-razor method may be applied to all embodiments of the present invention and results in a simultaneous or sequential or a combined simultaneous/sequential delivery of all included medicaments and optional excipients.

The invention claimed is:

1. A method of administering a metered dry powder combined dose of finely divided dry medication powders, comprising:

providing a relative motion between a nozzle of a dry powder inhaler and a dose bed carrying said combined dose of finely divided dry medication powder intended for delivery by the dry powder inhaler, the combined dose comprises metered quantities of at least two medicaments separately deposited on the dose bed, the relative motion causing the nozzle to pass over the combined dose for a simultaneous or sequential delivery of the medicaments during the course of a single suction of air.

2. The method according to claim 1, further comprising:

introducing the dose bed into the dry powder inhaler.

3. The method according to claim 1, further comprising:

delivering the medicaments by the dry powder inhaler (DPI) during the course of a prolonged delivery taking place in 0.01 to 6 s.

4. The method according to claim 1, wherein the at least two medicaments are selected from the following two medicament pairs:

Formoterol and Budesonide;
Formoterol and Ipratropium;
Formoterol and Fluticasone;
Formoterol and Tiotropium;
Ipratropium and Budesonide; and
Ipratropium and Salbutamol.

5. A dry powder inhaler comprising:

a nozzle;

a dose bed;

a combined dose of finely divided dry powders intended for delivery by the dry powder inhaler, the combined dose comprises metered quantities of at least two substances, separately deposited on the dose bed; and an arrangement for providing a relative motion between the nozzle and the dose bed, such that the nozzle passes over the combined dose for a simultaneous or sequential delivery of the substances during the course of a single suction of air and the relative motion.

6. The dry powder inhaler according to claim 5, further comprising a mouthpiece connected to the nozzle and adapted for receiving an applied air sucking effort.

7. The dry powder inhaler according to claim 5, wherein the nozzle is initially positioned outside an area of the dose bed onto which the substances are being deposited.

8. The dry powder inhaler according to claim 5, wherein the arrangement is arranged for providing the relative motion once an air stream induced in the nozzle exceeds a threshold flow velocity.

9. The dry powder inhaler according claim 5, wherein the dose bed is sealed with at least one foil and the dry powder inhaler further comprises an arrangement for opening the seal allowing the nozzle access to the dose bed.

10. The dry powder inhaler according to claim 9, wherein the dose bed comprises at least two compartments, the at least two substances are deposited in separate compartments and each compartment is provided with a separate seal to prevent interaction between separately deposited substances.

11. The dry powder inhaler according to claim 5, wherein at least one of the at least two substances is composed of a pure, chemical or biologic agent.

12. The dry powder inhaler according to claim 5, wherein at least one of the at least two substances is presented in form of a dry powder compound consisting of an effective amount of a pure, chemical or biologic agent mixed with suitable excipients.

13. The dry powder inhaler according to claim 5, wherein the dose bed is formed as a blister pack, where the dose bed is designed to accept separate deposits of the substances making up the pre-metered combined dose.

14. The dry powder inhaler according to claim 5, further comprising a biologically acceptable, inert substance deposited between the deposits of the at least two substances to prevent the at least two substances from detrimentally interact after forming of the combined dose.

15. The dry powder inhaler according to claim 5, wherein the at least two medicaments are selected from the following two medicament pairs:

Formoterol and Budesonide;
Formoterol and Ipratropium;
Formoterol and Fluticasone;
Formoterol and Tiotropium;
Ipratropium and Budesonide; and
Ipratropium and Salbutamol.

* * * * *